United States Patent [19]

Olson

[11] Patent Number: 4,817,643

[45] Date of Patent: Apr. 4, 1989

[54] CHINESE FINGER CUFF DENTAL FLOSS

[76] Inventor: Mary Lou C. Olson, 1147 Ivyhill Dr., Mendota Heights, Minn. 55118

[21] Appl. No.: 79,359

[22] Filed: Jul. 30, 1987

[51] Int. Cl.$^4$ ............................................. A61C 15/00
[52] U.S. Cl. ...................................... 132/329; 433/216
[58] Field of Search .................. 132/93, 91; 272/8 N, 272/8 R

[56] References Cited

U.S. PATENT DOCUMENTS

| | | | |
|---|---|---|---|
| 869,686 | 10/1907 | Bauno | 272/8 N |
| 1,839,486 | 1/1932 | Lawton | 132/93 |
| 3,247,857 | 4/1966 | Kaubar | 132/93 |

OTHER PUBLICATIONS

*The Textiles of Ancient Peru and Their Techniques* by Ravoul D'Harcourt, University of Washington Press.

*Sling Braiding of the Andes,* by Adell Cahlander, Weavers Journal Monograph (1980).
*Braiding Basics,* Exhibit A; and *Practical Braiding Techniques,* Exhibit B.

*Primary Examiner*—John Weiss
*Attorney, Agent, or Firm*—Merchant, Gould, Smith, Edell, Welter & Schmidt

[57] ABSTRACT

A dental floss woven in a chinese finger cuff pattern is provided. The dental floss is woven with a sufficient number of fibers to be self-supporting. The chinese finger cuff weave allows for constriction of the dental floss about its longitudinal axis when tension is applied in the longitudinal direction. The hollow cylinder defined by the chinese finger cuff weave may be filled with fluoride or other cleaning substances such that when the dental floss has longitudinal tension applied to it the fluoride is released. The interstitial spaces between the fibers provides for a trapping action of food particles when longitudinal tension is applied.

6 Claims, 1 Drawing Sheet

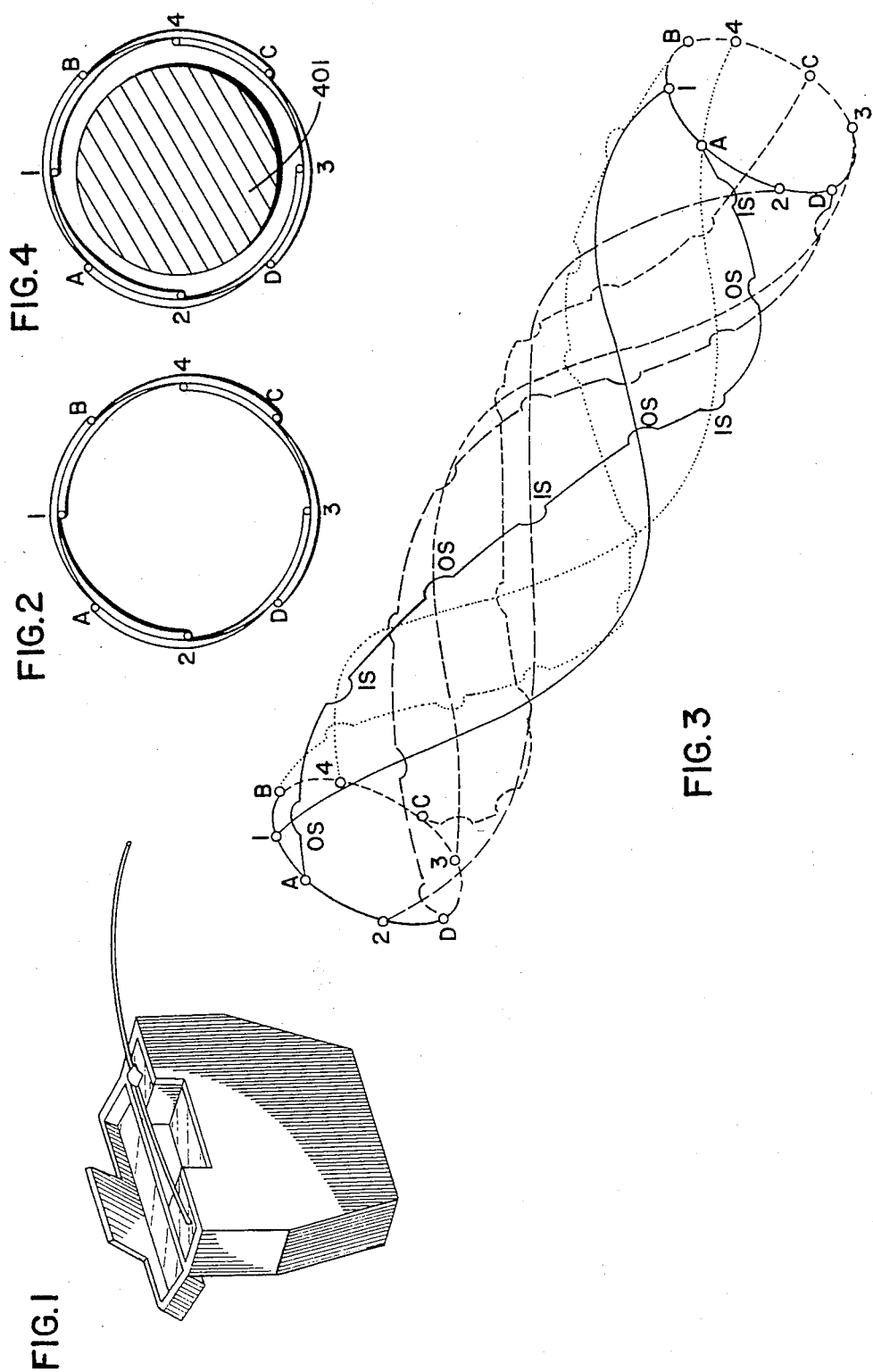

CHINESE FINGER CUFF DENTAL FLOSS

TECHNICAL FIELD OF THE INVENTION

The present invention pertains generally to the field of dentistry and more particularly to dental floss.

BACKGROUND OF THE INVENTION

Conventional dental floss consists of a plurality of woven fibers. Most conventional weaves, whether waxed or unwaxed, tend to separate and fray as the floss is passed between closely-spaced teeth. This fraying often leads to difficulty in accessing the space between closely spaced teeth, and can reduce the effectiveness of the flossing therebetween. Furthermore, the thickness of conventional floss often makes it difficult to work into the space between the sides of the teeth and the gums to remove food debris and plaque buildup.

SUMMARY OF THE INVENTION

The present invention provides a specially weaved dental floss which reduces its susceptibility to fraying and which has a thickness, or diameter, which can be controlled by the longitudinal tension applied thereto. In particular, the invention provides a dental floss using a Chinese fingercuff weave.

The primary benefit of this type of dental floss weave is that when tension is applied along the longitudinal axis, the cylinder defined by the helices of the weave becomes narrower and the weave reinforces itself against fraying and breaking. Thus, the floss of the present invention can be constricted to pass between tightly spaced teeth or to get at difficult to reach areas between the teeth and gums, while at the same time being resistant to fraying and breaking.

It is also contemplated that the Chinese fingercuff weave may provide a food particle trapping action as the weave tightens under tension. As the floss is pulled back and forth between teeth, the floss may trap food debris as the gaps between the fibers open and close as the tension on the floss fluctuates as its direction is reversed. This trapping action may allow for greater food particle removal, and more efficient flossing.

The invention also contemplates that the interior hollow of the floss weave could be filled with a chemical such as fluoride, or a fiber impregnated by fluoride, which would be forced out of the floss as it constricts during use. This action would allow a fresh flouride solution or other such chemical or paste to be applied to areas difficult to access by brushing.

BRIEF DESCRIPTION OF THE DRAWINGS

FIG. 1 is a view of a dispenser for the floss of the present invention;

FIG. 2 is an end view of dental floss woven according to the present invention;

FIG. 3 is an exploded view of a length of dental floss woven according to the present invention; and FIG. 4 is an end view of floss according to the present invention in which the cylinder is filled with a fluoride-impregnated fiber.

DETAILED DESCRIPTION OF THE PREFERRED EMBODIMENT

The dental floss according to the present invention is shown by an end view in FIG. 2. The floss consists of two sets of fibers, each set spiralling in an opposite direction. Each numeral or letter on FIG. 2 is positioned near the tip of the fiber. Fibers 1, 2, 3 and 4 are in Set 1, and spiral clockwise away from the viewer, while fibers A, B, C and D are in Set 2 and spiral counterclockwise away from the viewer. In this embodiment, eight fibers are used, four in each set. However, it can be readily seen that any number of fibers greater than two may be used, and each set need not have the same number of fibers. Changing the number of fibers, as well as the helical angle, will change the size of the gap when tension is not applied, and will also change the tension required to effectively close the gap between fibers.

FIG. 3 is an exploded view of the floss illustrating the Chinese fingercuff weave. It can be seen that fibers 1, 2, 3 and 4 are woven in a helical pattern, all spiralling in the same direction. Fibers A, B, C and D are also woven in a helical pattern; however, each spirals in the direction opposite to the spiral of fibers 1-4. FIG. 3 shows one complete revolution for each fiber; however, in actual usage, the floss is long enough to have each fiber complete numerous revolutions. Since the pattern simply repeats itself, understanding the weave of one revolution is sufficient.

The pattern that each fiber follows may be described as follows: a fiber in one set never crosses over or under a fiber in its own set; a fiber alternates crossing over and under fibers from the other set; a fiber never crosses any fiber in the other set twice before crossing each fiber once; and the order of crossing is the same for each fiber and one set and is repetitive. Thus, the path of fiber 1 may be described as spiralling away from the viewer in a clockwise direction, crossing under A, over D, under C, over B, under A, over D, under C, over B, and so on. The path for fiber 2 is described as spiralling away from the viewer in a clockwise direction, crossing under D, over C, under B, over A, and so on. Fibers 3 and 4 follow similar patterns, with fiber 3 starting by crossing under C, and fiber 4 starting by crossing under B.

The path that fiber A takes may be described as spiralling counterclockwise away from the viewer, crossing over 1, under 4, over 3, under 2, and so on. Fiber B spirals counterclockwise away from the viewer, crossing over 4, under 3, over 2, under 1, and so on. Fibers C and D follow similar paths, however fiber C starts by crossing over 3, and fiber D starts by crossing over 2.

The preferred embodiment uses fibers that are spaced evenly and wound with the same helical angle. This ensures that the size of the gaps is uniform throughout the floss. It is intended that floss may be woven using unequal spacing and each fiber having a unique helical angle, yet still be included in the scope and spirit of the claims.

FIG. 4 is an end view of dental floss woven according to the present invention. In this embodiment the hollow cylinder is filled with a flouride-impregnated fiber. When tension is applied along the longitudinal axis the cylinder narrows, causing pressure to be exerted on the inner fiber and forcing flouride solution out of the floss. It is also contemplated that the woven fibers themselves may contain flouride. The flouride would be forced out when tension is applied along the longitudinal axis.

Thus, there has been described a Chinese finger cuff weaver dental floss which has high strength, is resistant to fraying and which can be selectively constricted to access tight or narrow areas between the teeth or teeth and gums. The invention also provides for using the forces of the constricting weave to trap food particles or to release a chemical such as flouride from the fibers themselves or from the hollow interior space of the weave.

Although the invention has been described in its preferred form, those skilled in the art will recognize that various changes and modifications may be made thereto without departing from the spirit and scope of the invention as set forth in the claims appended hereto.

What is claimed is:

1. A dental floss comprising a plurality of fibers of a sufficient number to be self-supporting woven in a Chinese fingercuff pattern such that a hollow cylinder is defined by said fibers.

2. Dental floss according to claim 1 wherein said cylinder contains fluoride.

3. Dental floss according to claim 1 wherein said cylinder contains a fiber impregnated with fluoride.

4. Dental floss comprising:
   a first set of fibers, wherein said first set of fibers is comprised of a plurality of fibers;
   a second set of fibers, wherein said second set of fibers is comprised of a plurality of fibers;
   said first set of fibers woven in a cylindrical helical pattern such that each cylindrical helix defined by said fiber in said first set has a common axis, and equal radii, each of said cylindrical helices spiralling away from the viewer in a clockwise direction when viewed from either end;
   said second set of fibers woven in a cylindrical helical pattern such that each cylindrical helix defined by each of in said second set of fibers has the said common axis of said first set of fibers and a radius equal to the said radius of first set of fibers, furthermore each of said cylindrical helices spiral away from the viewer in a counterclockwise direction when viewed from either end.

5. Dental floss according to claim 4 wherein said cylinder contains fluoride.

6. Dental floss according to claim 4 wherein said cylinder contains a fiber impregnated with fluoride.

* * * * *

UNITED STATES PATENT AND TRADEMARK OFFICE
CERTIFICATE OF CORRECTION

PATENT NO. : 4,817,643

DATED : April 4, 1989

INVENTOR(S) : Mary Lou C. Olson

It is certified that error appears in the above-identified patent and that said Letters Patent is hereby corrected as shown below:

Col. 1, line 48, "flouride" should be --fluoride--.

Col. 2, line 38, after "B." insert --In Fig. 3, "OS" means "outside" while "IS" means "inside", to denote under and over paths of the crossing fibers.--

Col. 2, lines 56, 59 and 61 (in both instances), "flouride" should be --fluoride--.

Col. 3, line 2, "flouride" should be --fluoride--.

Col. 4, line 11, "in said second set of fibers" should be --said fibers in said second set--.

Signed and Sealed this

Twenty-sixth Day of February, 1991

Attest:

HARRY F. MANBECK, JR.

*Attesting Officer*  *Commissioner of Patents and Trademarks*